United States Patent
Ribble et al.

(10) Patent No.: US 7,960,326 B2
(45) Date of Patent: *Jun. 14, 2011

(54) EXTRUDED CLEANSING PRODUCT

(75) Inventors: Brendon F. Ribble, Menasha, WI (US); Sarah L. Christoffel, Appleton, WI (US); Catherine M. Hancock-Cooke, Neenah, WI (US); Robert C. Hochholzer, Kimberly, WI (US); John E. Kerins, Neenah, WI (US); Michael J. Nelson, Neenah, WI (US); Timothy J. Probst, Neenah, WI (US); Joseph R. Riegert, Black Creek, WI (US); Marci E. Sojka, Neenah, WI (US); Emil Stavinoha, Sr., Castroville, TX (US); Vickie M. Thomack, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 325 days.

This patent is subject to a terminal disclaimer.

(21) Appl. No.: 10/236,017

(22) Filed: Sep. 5, 2002

(65) Prior Publication Data

US 2004/0048759 A1 Mar. 11, 2004

(51) Int. Cl.
*A61K 7/50* (2006.01)
(52) U.S. Cl. ........ 510/130; 510/141; 510/156; 510/424; 510/474
(58) Field of Classification Search .................. 510/389, 510/451, 454, 474, 481
See application file for complete search history.

(56) References Cited

U.S. PATENT DOCUMENTS

| 3,669,891 A | 6/1972 | Greenwood et al. |
| 4,013,475 A | 3/1977 | Liebowitz et al. |
| 4,082,682 A | 4/1978 | Inamorato et al. |

(Continued)

FOREIGN PATENT DOCUMENTS

EP 0266124 A2 5/1988

(Continued)

OTHER PUBLICATIONS

CDC (Rev. By Julia S. Garner, R.N., M.N. and Martin S. Favero, Ph.D.); *Guideline for Handwashing and Hospital Environmental Control*, 1985, pp. 1-27.

(Continued)

*Primary Examiner* — Necholus Ogden, Jr.
(74) *Attorney, Agent, or Firm* — Dority & Manning, P.A.

(57) ABSTRACT

The present invention is directed to a personal cleansing product which can be sized as a single use personal cleansing product. The cleansing product is an extruded foam product which can disintegrate upon contact with water when used in the standard fashion to wash. As the foam disintegrates, the cleansing agent held in the foam matrix is released. The disintegration of the product can take place slowly, over a period of time such that when an individually sized cleanser is used to scrub until it completely disintegrates, scrubbing duration is long enough to ensure desired levels of cleanliness have been attained. Alternatively, the product can disintegrate immediately, and release all of the soap at essentially one time. The product is an extruded foam expanded from a mixture of a natural starch, a nucleating agent, a water soluble disintegrant, a blowing agent, a water soluble polymer, and a soap base. Optionally, the foam can include a destructured starch, natural, dyes, fragrances, and the like to obtain specific product characteristics.

37 Claims, 2 Drawing Sheets

U.S. PATENT DOCUMENTS

| | | | |
|---|---|---|---|
| 4,102,995 | A | 7/1978 | Hebborn |
| 4,111,853 | A | 9/1978 | Shultz et al. |
| 4,335,103 | A | 6/1982 | Barker et al. |
| 4,532,132 | A | 7/1985 | Keil |
| 4,704,224 | A | 11/1987 | Saud |
| 4,954,544 | A | 9/1990 | Chandaria |
| 4,999,348 | A | 3/1991 | Cioca et al. |
| 5,021,183 | A | 6/1991 | Saud |
| 5,064,635 | A | 11/1991 | Casey |
| 5,215,757 | A | 6/1993 | El-Nokaly |
| 5,246,614 | A | 9/1993 | Baumgartner et al. |
| 5,266,321 | A | 11/1993 | Shukuzaki et al. |
| 5,272,181 | A | 12/1993 | Boehmer et al. |
| 5,304,334 | A | 4/1994 | Lahanas et al. |
| 5,427,708 | A | 6/1995 | Stark |
| 5,447,962 | A | 9/1995 | Ajioka et al. |
| 5,486,228 | A | 1/1996 | Miller et al. |
| 5,502,158 | A | 3/1996 | Sinclair et al. |
| 5,569,692 | A | 10/1996 | Bastioli et al. |
| 5,597,556 | A | 1/1997 | Moghe et al. |
| 5,599,555 | A | 2/1997 | El-Nokaly |
| 5,606,016 | A | 2/1997 | Maeda et al. |
| 5,614,564 | A | 3/1997 | Hwang et al. |
| 5,626,853 | A | 5/1997 | Bara et al. |
| 5,645,822 | A | 7/1997 | Meyer et al. |
| 5,688,831 | A | 11/1997 | El-Nokaly et al. |
| 5,714,230 | A | 2/1998 | Kameoka et al. |
| 5,756,438 | A * | 5/1998 | Rau et al. .................... 510/151 |
| 5,763,098 | A | 6/1998 | Kameoka et al. |
| 5,852,114 | A | 12/1998 | Loomis et al. |
| 5,876,995 | A | 3/1999 | Bryan |
| 5,891,428 | A | 4/1999 | Greff |
| 5,906,783 | A | 5/1999 | Narayan et al. |
| 6,018,033 | A | 1/2000 | Chen et al. |
| 6,113,886 | A | 9/2000 | Bryan |
| 6,120,803 | A | 9/2000 | Wong et al. |
| 6,152,358 | A | 11/2000 | Bryan |
| 6,174,535 | B1 | 1/2001 | Lundmark |
| 6,184,261 | B1 | 2/2001 | Biby et al. |
| 6,194,517 | B1 | 2/2001 | Pomplun et al. |
| 6,224,852 | B1 | 5/2001 | Morgan et al. |
| 6,228,822 | B1 | 5/2001 | Allison et al. |
| 6,247,995 | B1 | 6/2001 | Bryan |
| 2003/0017959 | A1 | 1/2003 | Baeck et al. |

FOREIGN PATENT DOCUMENTS

| | | |
|---|---|---|
| EP | 0284765 B1 | 10/1988 |
| EP | 0418049 A2 | 3/1991 |
| EP | 0418049 A3 | 3/1991 |
| EP | 0850039 B1 | 7/1998 |
| FR | 2717184 | 9/1995 |
| FR | 2805162 A1 | 8/2001 |
| GB | 2056902 A | 3/1981 |
| GB | 2349649 A | 11/2000 |
| WO | WO 9629047 A1 | 9/1996 |
| WO | WO 9632924 A1 | 10/1996 |
| WO | WO 0119946 A1 | 3/2001 |
| WO | WO 0124990 A1 | 4/2001 |
| WO | WO 0125390 A2 | 4/2001 |
| WO | WO 0125390 A3 | 4/2001 |

OTHER PUBLICATIONS

E. L. Larson and 1992, 1993, and 1994 APIC Guidelines Committee Assn. For Professionals in Infection Control and Epidemiology, Inc., *APIC Guideline for Hand Washing and Hand Antisepsis in Health-Care Settings*, 1995, pp. 1-17.

Product Description—BASF Jordapon® Cocoyl Isethionates, 1 page.

Product Description—Nacconol 90G, Stepan Co., 1998, 1 page.

Article—*Development of A Low Cost, Environmentally Friendly, Starch-Based Packaging*, Feb. 2001 4 pages.

PCT Search Report, Jan. 21, 2004.

US 6,290,977, 09/2001, Friars et al. (withdrawn)

* cited by examiner

EXTRUDED CLEANSING PRODUCT

BACKGROUND OF THE INVENTION

One of the most effective methods found to date for limiting the spread of communicable disease is through effective personal cleaning, particularly through thorough hand washing. Thorough hand cleaning includes not only washing often with a suitable cleanser, but also washing for a period of time long enough to ensure sanitary conditions have been attained.

Many soaps and other detergent cleansers can provide the desired levels of hygiene if used correctly. However, these cleansers are usually supplied to the public in bar or liquid form, and people, particularly children, often give only a cursory wash, and therefore don't clean as thoroughly as required to remove dirt, grime and/or disease causing agents.

In one attempt to address such problems, liquid cleansers have been developed which change color after a certain amount of time spent scrubbing. Such cleansers tend to be expensive, however, and are primarily directed toward medical applications, such as surgical scrubbing applications. Thus, a need exists for a cleaning product which can be moderately priced and encourage desired scrubbing time, even when used by children.

Another problem experienced with cleansers today involves difficulties in handling the cleanser as well as the unsightliness around the sink area caused by the cleansers themselves. For example, when using a bar soap, not only can the bar itself become unsightly as it is used slowly over time, but soap residue on the soap dish or tray and the sink itself can also build up, causing an unsightly mess. Bar soaps are also notoriously slippery and difficult to hold onto when wet. Liquid cleansers also can cause problems. For example, inadvertent release of excess cleanser from the dispenser can lead not only to soap building up in and around the sink, but also on the bottle itself, causing the bottle to become slick and difficult to hold as well as messy. Liquid cleanser dispensers also tend to become clogged, due to build up of the liquid at the dispenser outlet.

As such, a further need exists for a cleanser which can be delivered to the consumer in a form which can provide the desired cleaning action without causing untidiness in or around the sink.

Expanded foam is a material which has been used to produce a large variety of articles. For example, expanded polystyrene foam has been used to form packing material and light weight disposable articles such as plates, cups, serving trays, etc. Recently, foams have been developed which are more environmentally friendly, i.e. biodegradable, than the petroleum based foams of the past. In certain instances, these biodegradable foams can include a destructured starch.

Destructured starch is starch which has had the crystalline structure destroyed and has become thermoplastic in nature. A starch can be destructured by various methods involving combinations of pressure, heat, and mechanical work in the presence of plasticizers and/or destructuring agents such as urea and alkaline hydroxides. For example, starch can be heat treated above the glass transition temperature and melting points of its components, generally above about 120° C., in the presence of destructuring agents to become destructured starch. For additional information concerning destructured starch, see, for example, U.S. Pat. No. 5,569,692 to Bastioli, et al. which is incorporated herein by reference as to all relevant matter.

U.S. Pat. No. 6,184,261 to Biby, et al. which is incorporated herein by reference as to all relevant matter, discloses a water-resistant degradable foam that is an extrudate of a mixture of a thermoplastic polymer, destructured starch, and a plasticizer.

The present invention provides an extruded cleansing product formed of an expanded foam material that overcomes problems with cleansers of the past. In certain embodiments, the foam matrix can include a destructured starch.

SUMMARY OF THE INVENTION

In one embodiment, the present invention is directed to a novel personal cleansing product. For example, the personal cleansing product can be an extruded cleansing product which can disintegrate as it is used in conjunction with water to clean. As the product disintegrates, it can release a cleanser. In one embodiment, before the product disintegrates completely, it can provide a timed or time controlled duration of scrubbing which can ensure desired levels of cleanliness after use.

In general, the extruded cleansing product of the present invention can be formed from a mixture which includes a natural starch, a water soluble disintegrant, a soap base, a water soluble polymer, a nucleating agent, and a blowing agent. The mixture can be extruded to form the expanded foam of the invention. As the foam disintegrates during the washing process, the soap base can be released from the foam.

The water soluble disintegrant can be a dextrin, such as maltodextrin for example. In one embodiment, from about 20% to about 65% by weight of the components fed to the extruder can be a water soluble disintegrant.

In one embodiment, the blowing agent can be an alcohol, such as ethanol. Generally, from about 5% to about 10% by weight of the mixture in the extruder can be a blowing agent.

The soap base can be any desired soap base known in the art which can be extruded with the other components. For example, a fatty acid soap or other types of surfactant detergents, such as synthetic detergents, can be used as the soap base which is delivered as the foam disintegrates. The mixture in the extruder can generally include between about 10% to about 30% by weight soap base.

A water soluble polymer is also included in the mixture which is extruded to form the expanded foam product of the present invention. In one embodiment, the water soluble polymer can be a water soluble thermoplastic polymer such as, for example, polyvinyl alcohol. In general, the mixture can include between about 5% and about 10% water soluble polymer.

The mixture can also include between about 5% and about 10% by weight nucleating agent. In one embodiment, the nucleating agent can be talc, for example a food grade talc.

The mixture also can include a natural starch. In one embodiment the mixture in the extruder can be between about 3% and about 10% natural starch.

Optionally, other additives can be included in the mixture to be extruded. For example, up to about 25% of the mixture in the extruder can be a destructured starch, if desired.

Other possible additives to the mixture can include additives generally known in the art such as, for example, dyes, fragrances, emollients, antioxidants, vitamins, etc. Moreover, desired additives can be either added directly to the mixture or optionally can be encapsulated, such that they are released later, for example when the product is used in the presence of water and/or under pressure due to scrubbing action.

In one embodiment, the cleansing product can be an abrasive cleansing product and abrasion enhancing additives can be included in the mixture to be extruded.

As the product is used to clean, the foam can disintegrate and release the soap base. In one embodiment, the time for disintegration can be less than about 2 minutes. The disintegration can be triggered by contact time with water, water temperature, scrubbing pressure, or any combination of the three.

In another possible embodiment, the present invention is directed to a process for producing an extruded cleansing product. In general, the process includes combining a variety of components to form a mixture and then expanding the mixture by passage through an extruder to form a foam. For example, in one embodiment, between 0% and about 25% by weight destructured starch, between about 20% and about 65% by weight water soluble disintegrant, between about 10% and about 30% by weight soap base, between about 5% to about 10% by weight water soluble thermoplastic polymer, between about 5% and about 10% by weight nucleating agent, between about 3% and about 10% natural starch, and between about 5% and about 10% by weight alcohol can be mixed and then expanded to form an extruded cleansing product.

The components can be mixed in a mixer, such as a Hobart® mixer, for example, and then transferred to the extruder, or alternatively can be added directly to the extruder and mixed within the extruder, as desired. Any suitable extruder can be used, for example, either a single screw or a twin screw extruder can be used. For instance, a conical twin screw extruder can be used in the process. In one embodiment, a co-extrusion process can be used, and the foamed product can include zones of different materials.

In general, the extruder can operate at a screw speed of between about 50 and about 250 rpm. Additionally, the feed zone of the extruder can be between about 80° C. and about 130° C. and the nozzle temperature of the extruder can be between about 100° C. and about 175° C.

The extruded cleansing products of the present invention can be of any desired shapes and orientations. For example, relatively flat shapes or alternatively more three dimensional shapes can be formed. In one embodiment, several individual foamed product pieces can be attached together to form a conglomerate of individual products which together form a large structure.

BRIEF DESCRIPTION OF THE FIGURES

A full and enabling disclosure of the present invention, including the best mode thereof to one of ordinary skill in the art, is set forth more particularly in the remainder of the specification, including reference to the accompanying figures in which.

Repeat use of reference characters in the present specification and drawings is intended to represent same or analogous features or elements of the present invention.

DETAILED DESCRIPTION

Reference now will be made in detail to embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to a novel personal cleansing product. More specifically, the present invention discloses an extruded cleansing product and a process for producing the extruded cleansing product. The extruded cleansing product can be an extruded foam that can disintegrate while in contact with water as it is used to scrub the hands, face, body, etc.

In one embodiment, the product can be sized for a single use. In this embodiment, as the product is used to wash, the foam product can disintegrate. In this embodiment, the washing process can continue until the product has completely disintegrated. The product can be specifically designed for a desired period of disintegration, depending upon the desired product characteristics. For example, the product can be designed to disintegrate relatively slowly, such as over a period of about 2 minutes or longer, in those embodiments wherein a longer, more thorough scrubbing time is desired, such as medical applications. Alternatively, the product can be designed to disintegrate in a shorter amount of time, down to an essentially immediate disintegration, in those embodiments where a quick wash is desired. In general, the extruded cleanser of the present invention can disintegrate when in contact with water and/or scrubbing pressure in less than about 2 minutes.

The extruded cleansing product of the present invention generally includes a foam formed of a disintegrant, a water soluble polymer, a nucleating agent, a natural starch, and a soap base, which are mixed and then expanded with a blowing agent via an extrusion process to form a foam matrix. In one embodiment, the mixture can also include a destructured starch.

The relative amounts of the components can vary depending on the desired product characteristics. For example, the relative amounts of destructured starch and the disintegrant can be balanced to not only aid in control of the rate of disintegration of the foam, but also to influence the quantity and size of any foam particles remaining after disintegration. Other components can optionally be included in the foam to further refine the characteristics of the product, such as the disintegration characteristics for instance. Other optional additives, in addition to destructured starch, can include, for example, dyes, vitamins, emollients, abrasive enhancing additives, encapsulated additives, and the like, which can impart desired qualities to the cleansing product.

As the foamed product disintegrates, the various components can either dissolve completely and be washed away with the wash water, or can be in small enough particles after disintegration to flow with the water and enter the sewage system without causing harm to drains or waste water treatment facilities. The relative amounts of the different components and the overall formulation of the product can be varied to affect disintegration rate. For example, the cleaning product can be designed to disintegrate based upon time of contact with water, temperature of the contact water, pressure due to the scrubbing motion, or some combination thereof. The relative amounts of components as well as the optional additives included in the product can be varied to obtain the desired disintegration characteristics. The component make-up can also affect other characteristics of the cleanser such as grittiness during use, color, odor, and texture of the foam, for example.

The cleansing product is an expanded foam product such as can be produced through an extrusion process. In general, this involves combining the various components until well mixed and extruding through a nozzle. The extrudate expands as it exits the nozzle and the foamed product is thus produced. The foamed product can be formed into any desired shape. For example, a relatively flat sheet of extrudate can exit the extruder which can then be further processed. In one embodiment, flat shapes such as stars, fish, cartoon characters or any other shape can be punched from a flat sheet of extrudate. Such shapes can be further defined or enhanced, if desired, such as with an embossing process. Alternatively, a more three dimensional foam, such as an endless cylindrical rod can be formed at the nozzle. This can then be cut or otherwise shaped into more three dimensional product shapes such as balls, crayon-shaped cylinders, cloud puffs, popcorn, candy shapes, and the like. Three dimensional forms can also be created by molding the extrudate, for example by injection molding the extrudate.

The foamed product of the present invention can include a water-soluble thermoplastic polymer which is added to the extruder mixture. In one embodiment, a water-soluble thermoplastic polymer such as polyvinyl alcohol can be added to the mixture as a solid and extruded with the other components of the foamed cleanser. For example, the polyvinyl alcohol can be added in solid form with average particle diameter less than about 100 micrometers. In one embodiment, polyvinyl alcohol with an average particle diameter of between about 40 and about 90 micrometers can be added to the mixture. A water-soluble thermoplastic polymer can impart certain desired qualities to the foam such as, for example, improved compressibility and plasticity of the dry product, and faster and more complete disintegration of the foam. In general, a water soluble polymer can make up between about 5% and about 10% by weight of the extruder mixture. In one embodiment, the water soluble polymer can make up about 7.7% by weight of the mixture.

In order to disintegrate as desired in the presence of water, the foam can include a disintegrant. A disintegrant can be any non-polymeric water soluble component which can interfere with cross-linking of the polymers forming the foam matrix. In one embodiment, dextrin can be added to the mixture as a disintegrant. Other disintegrants are possible, however, such as, for example, sugars, such as mannitol, sorbitol, sucrose, lactose, fructose, maltose; salts such as sodium chloride, potassium chloride, calcium sulfate; the amino acids alanine, arginine, asparagine, aspartic acid, cysteine, glutamic acid, glutamine, glycine, histidine, isoleucine, leucine, lysine, methionine, phenylalanine, proline, serine, threonine, tryptophan, tryosine, and valine; buffering agents such as citric acid, sodium citrate, potassium citrate, succinic acid, fumaric acid, sodium acetate, sodium phosphate monobasic, tartaric acid, sodium potassium tartrate; surface active agents such as poloxamers, polysorbates, lecithin and the like; and effervescing couples such as citric acid blended with sodium bicarbonate, and similar blends. Malodextrin, having a molecular weight of about 400 to 4000 grams per mole, is one example of a low molecular weight polymeric material useful as a disintegrant in this invention.

In one embodiment of the present invention maltodextrin having an average particle diameter of less than about 100 micrometers can be used as the disintegrant. More specifically, maltodextrin having an average particle diameter between about 40 micrometers and about 90 micrometers can be used, though larger disintegrants can alternatively be added to the extruder mixture.

The amount of the disintegrant in the cleansing product can be adjusted to obtain desired disintegration characteristics in the final foamed product. For example, increasing the amount of disintegrant while not including any destructured starch in the mixture can create a product which can disintegrate essentially upon contact with water, releasing the soap base from the foam very quickly. Conversely, lesser amounts of disintegrant can be used, such as in those embodiments wherein the product disintegrates more slowly, requiring the user to wash more vigorously or for a longer period of time before the single use product is completely disintegrated and all of the soap base is released from the foam. In one embodiment, between about 20% and 65% by weight of the mixture to be extruded can be a disintegrant. In one embodiment, between about 30% and about 50% by weight of the mixture can be a disintegrant. In one embodiment, the disintegrant can make up about 38.5% by weight of the extruder mixture.

The soap base delivered to the user as the foam disintegrates can be any suitable soap base and can be designed or chosen with specific product use in mind. For instance, any desired soap base ranging from an aggressive, antiseptic soap as is used in a clinical setting, to a gentle, mild detergent for use on sensitive skin, can be delivered to the user as the foam disintegrates. For example, the soap base can be a soap, such as a fatty acid soap. Alternatively, the soap base can be any other detergent known to be applicable in personal cleansing products. For example, surfactant systems as are known in the art can be used as the desired soap base. Possible surfactants or surfactant systems can include known anionic, nonionic, zwitterionic or amphoteric surfactants. In one embodiment, synthetic detergent preparations can be used as the soap base. For instance, synthetic detergent systems including sodium cocoyl isethionate, sold as Jordapon® CL prilled isethionate surfactants available from the BASF Corporation, sodium dodecylbenzene sulfonate, sold under the name Nacconol® by the Stepan Company, or sodium olefin sulfonate sold as Bio-Terge® obtainable from the Stepan Company, can be suitable soap bases in the cleansing product of the present invention. As desired, either a single soap base can be used, or alternatively a combination of different soap bases can be used together in the cleansing product.

Generally, the soap base of the present invention can make up from about 10% to about 30% by weight of the mixture in the extruder. More specifically, the soap base component of the mixture can be from about 15% to about 25% by weight of the mixture. In one embodiment, the extruder mixture can include about 22.1% by weight soap base.

The mixture in the extruder can also contain a blowing agent. The blowing agent can either be a gas or a liquid which is superheated in the extruder. The blowing agent functions to expand the product and help to form the foam as it exits the extruder nozzle. For example, a liquid blowing agent can be superheated by compression of the extruder screw and cause expansion of the foam at the nozzle. Cell size and amount of total expansion can be affected by the amount and characteristics of the blowing agent added to the mixture. In the past, water has primarily been the liquid blowing agent of choice in foam forming technology. However, in the present invention, due at least in part to the presence of the soap base in the product, blowing agents other than water are preferred to obtain desired expansion of the foam. For example, blowing agents including various gases such as carbon dioxide can be introduced to the extruder just prior to final extrusion at the nozzle.

Alternatively, a liquid blowing agent, such as an alcohol, can be added to the mixture in the extruder. For example, ethanol can be used as a liquid blowing agent added to the extruder mixture. In one embodiment, from about 5% to about 10% by weight of the mixture in the extruder can be a liquid blowing agent, such as, for example, ethanol. In one embodiment, the mixture can include about 7.7% blowing agent.

The cleansing product of the present invention can also included a natural starch in the matrix. Natural starch is somewhat soluble in water, and as such can aid in disintegration of the cleanser during use. In one embodiment, when quick, temperature based disintegration of the foam carrier is desired, it may be beneficial to increase the amount of natural starch in the extruder mixture.

In general, the mixture can include between about 2% and about 10% natural starch. In one embodiment, mixture can be about 3.8% by weight natural starch. In addition to affecting disintegration characteristics of the product, natural starch has inherent expansion characteristics upon extrusion and can also help give the foam a fairly rigid structure.

The natural starch used can be any starch of natural or plant origin. For example, starch extracted from plants such as corn, wheat, potato, rice, sorghum, tapioca, or various grains can be used. Generally, a natural starch can be granulated into particles before it is mixed with the other components of the cleansing product. For example, natural starch can be granulated into particles having an average particle diameter of less than about 100 micrometers prior to being mixed with the other components. In one embodiment, the starch can be granulated to an average particle diameter of between about 40 micrometers and about 90 micrometers.

The foamed cleanser can also contain a nucleating agent. Nucleating agents are small particulate materials which can initiate the development of air cells and can help to control the cell size formed in the foam. A nucleating agent can also improve the texture of the foam and provide the dry foam with a smoother surface. In general, the mixture can be between about 5% and about 10% by weight nucleating agent. In one embodiment, the mixture can be about 7.7% nucleating agent. In one embodiment, a nucleating agent can be a food grade talc. For example, food grade talc having an average particle diameter of less than about 300 micrometers can be used. In one embodiments, talc having an average particle diameter between about 50 and about 200 micrometers can be used. The nucleating agent need not be food grade talc, for example, in one embodiment, the nucleating agent can be any grade talc which will not present a health hazard when used with a cleanser in expected practice.

Optionally, the foam can include destructured starch. The destructured starch component of the product can be from any starch of natural or plant origin which is composed essentially of amylose and/or amylopectin. The starch can be extracted from any suitable plant, such as, for instance, potatoes, rice, maize, tapioca, or various cereals, such as rye, wheat, oats, etc. Chemically modified starches and starches of different genotypes can also be used, if desired. Additionally, ethoxy derivatives of starch, starch acetates, cationic starches, oxidized starches, cross-linked starches and the like may also be used. The destructured starch which is added to the extruder mixture can have an average particle size of any suitable diameter. For example, the destructured starch can have an average particle size greater than about 300 micrometers. In one embodiment, the destructured starch can have an average particle diameter between about 300 micrometers and about 1 millimeter.

Destructured starch can become highly cross-linked in the foam product and can aid in maintaining the open structure of the extrudate after expansion. Being highly cross-linked, it can also be more resistant to dissolution in water than natural starch, and can be slower to disintegrate than other components of the cleansing product. As such, the greater the amount of destructured starch in the product, the slower the foam can disintegrate. Therefore, when producing a product in which a longer duration of scrubbing prior to disintegration is desired, it may be beneficial to increase the amount of destructured starch in the mixture which will be extruded to form the foam. Additionally, as the foam breaks down and disintegrates during scrubbing, small particles of destructured starch can maintain their integrity. The greater the amount of destructured starch in the foam, the larger and more numerous these remaining particles can be. As such, certain embodiments of the invention, in which a more abrasive cleansing product is desired, can include relatively high levels of destructured starch in the foam mixture.

Generally, up to about 25% by weight of the mixture in the extruder can be destructured starch, depending on the characteristics desired in the final product. In one embodiment, the mixture in the extruder can comprise between 0% and about 23% destructured starch. In one embodiment the mixture in the extruder can include about 20.3% destructured starch.

Other additives can also be included in the cleansing product of the present invention as desired. For example, dyes, emollients, fragrance, oils, vitamins, pH adjusters, antimicrobial agents, antioxidants, and the like can be included in the cleanser. In addition, certain embodiments of the invention can include various additives to increase the abrasiveness of the cleanser. For example, abrasive enhancing particulates, such as microspheres or other granules such as pumice or silica can be included in the cleanser.

Microspheres can be from about 10 micrometers to about 1 mm in diameter and typically have a shell thickness of from about 1 to about 5 micrometers, while macrospheres (which can also be used in some embodiments) can have diameters greater than about 1 mm. Such materials can include microbeads of metal, glass, carbon, mica, quartz or other minerals, plastic such as acrylic or phenolic, including acrylic microspheres known as PM 6545 available from PQ Corporation of Pennsylvania, and hollow microspheres such as the cross-linked acrylate SunSpheres™ of ISP Corporation (Wayne, N.J.) and similar hollow spheres as well as expandable spheres such as Expancel® microspheres (Expancel, Stockviksverken, Sweden, a division of Akzo Nobel, Netherlands), and the like.

The cleansing product can also be formulated with additives which can change the characteristics of the product as it disintegrates. For example, encapsulated additives can be added to the mixture. Encapsulated additives can be released as a function of time, temperature, and/or pressure during the scrubbing process. Possible encapsulated additives can include, for example, dyes, emollients, or fragrances. Additionally, time delayed additives which possess an interval for change after contact with water can be included such that product characteristic such as the color or the fragrance, for example, change as the product disintegrates with use. The trigger for such time delayed changes can be tied to changes encountered during use such as, for instance, temperature changes, pressure variations, pH changes, mixing of different components during scrubbing, and the like.

In one embodiment, the mixture added to the extruder to form the extruded cleansing product of the present invention can include between 0% to about 25% destructured starch, about 20% to about 65% by weight dextrin, about 10% to about 30% by weight synthetic detergent, about 5% to about 10% by weight ethanol, about 5% to about 10% by weight food grade talc, about 5% to about 10% by weight polyvinyl alcohol, about 2% to about 10% by weight natural starch and up to about 5% by weight fragrance.

Figure 1:
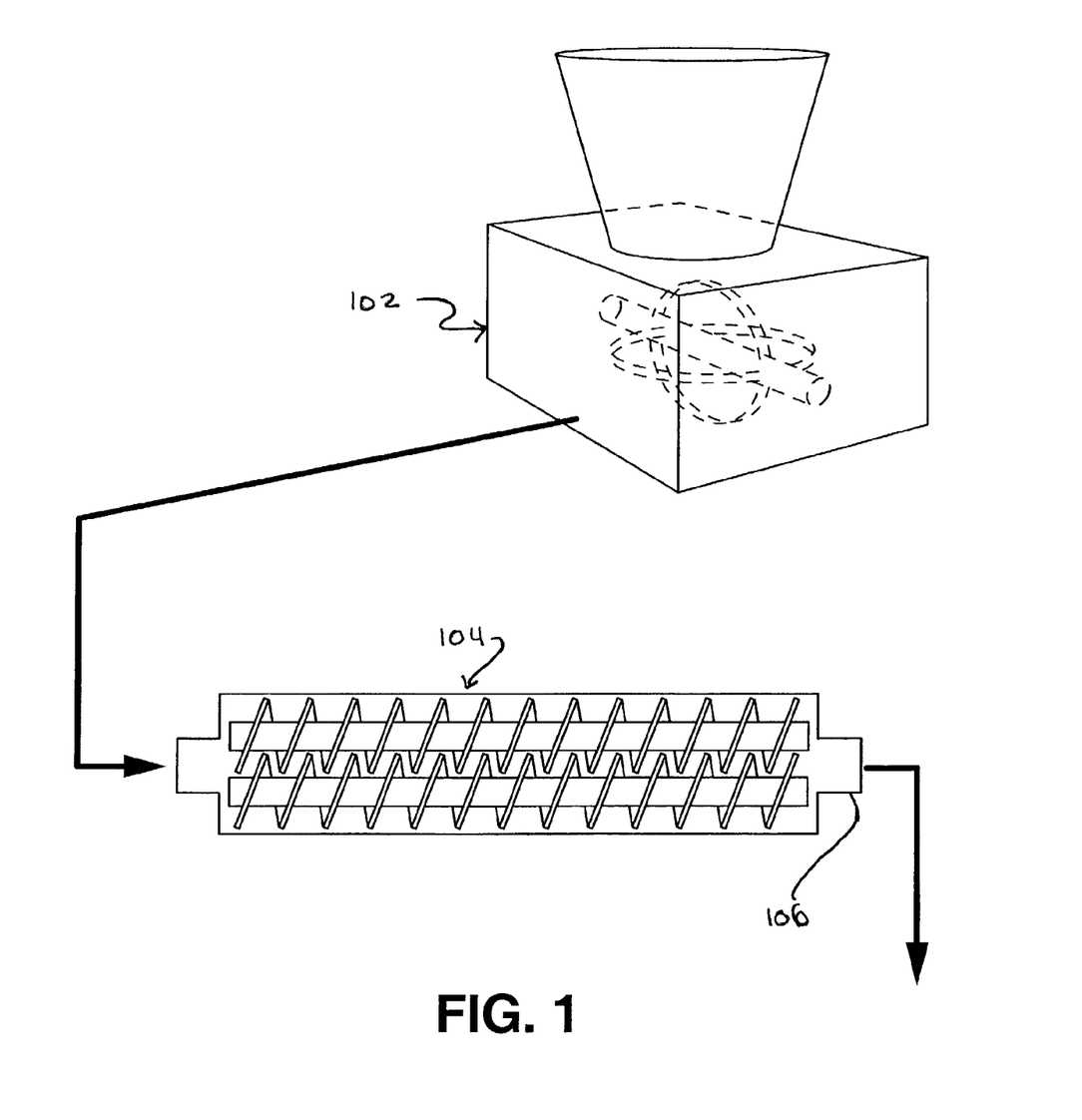
FIG. 1 is one embodiment of a process for producing the extruded cleansing product of the present invention.

FIG. 1 illustrates one possible embodiment of a process for forming the extruded cleansing product of the present invention. In this embodiment, the components which can be expanded via the extruder 104 can first be combined in a mixer 102. Any suitable mixer can be used to combine the component ingredients of the mixture. For example, in one embodiment a double ribbon mixer 102, as illustrated in FIG. 1, can be used. Other styles of mixers could alternatively be used, however. For example, a food mixer such as those sold by the Hobart® corporation could be used. In one embodiment, a Hobart® Model A120-2 mixer can be used to mix the components prior to the mixture being fed to an extruder. Alternatively, a separate mixing step can be avoided, and the components can be added directly to the extruder for mixing within the extruder itself prior to expansion at the nozzle.

There is no particular order by which the components must be added to the mixer or the extruder. The mixer can be run at ambient temperature for a long enough period to thoroughly mix all of the components. For example, the components can be mixed in the mixer 102 for a time between about 1 minutes and about 15 minutes to obtain the desired extruder feed. The extruder feed can usually be quite dry. For example, the extruder feed can have a moisture content of between about 4% and about 10%. In one embodiment, the extruder feed can have a moisture content of between about 7.24% and about 7.41%.

The extruder feed can usually be fed through the extruder 104 by means of a screw feed, though this is not required in the present process. For example, the extruder can be a single screw extruder such as those available from the Randcastle Corporation, or a twin screw extruder such as those available, for example, from the Wanger or Brabender Corporations.

In one embodiment, a twin screw extruder, such as, for example, a conical twin screw extruder, can be used. A conical twin screw extruder can thoroughly mix the feed and provide a foam with a very uniform structure.

When a screw extruder is used for the present process, whether a single or twin screw extruder is used in the process, the screw speed can generally be between about 50 and about 250 rpm, more specifically between about 100 and about 200 rpm. The residence time of the mixture in the extruder can be between about 15 seconds and about 2 minutes.

Typically, an extruder can be described with four zones, a feed zone, a metering zone, a compression zone and a die section. In the present invention, the feed zone can generally have a temperature of between about 80° C. and about 145° C., more specifically about 100° C. The remaining zones can be at a higher temperature, such as between about 100° C. and about 175° C. Higher temperatures than about 175° C. could cause components of the foam to char and should be avoided. In one embodiment, the temperature at the nozzle 106 of the can be about 165° C. As the mixture passes through the extruder, it becomes pressurized to between about 300 psi and about 1500 psi. Once the mixture exits the hot extruder and enters into ambient temperature and pressure, it can expand and form a foam.

The amount of expansion obtained in the foam upon exit from the extruder can depend upon a combination of several factors. For example, the amount of the blowing agent added to the mixture can affect the amount of expansion. Additionally, the amount of the other components added to the mixture, the temperature and pressure profile of the extruder, and the extruder screw speed can all affect expansion characteristics of the foam. Greater expansion in the foam as it exits the extruder tends to provide a cleansing product with more complete disintegration upon use, i.e., a single-use sized product which can disintegrate and leave little or no particles of product when combined with water and scrubbing action for a period of time.

In those embodiments wherein the extruder nozzle 106 is round, expansion values can be obtained merely by comparing the nozzle diameter to the foam diameter after expansion. Equivalent means can be utilized for other nozzle shapes. Generally, the cleansing products of the present invention can exhibit at least about 140% expansion upon extrusion. In one embodiment, the cleansing products can exhibit between about 140% and about 550% expansion upon extrusion.

Figure 2A:
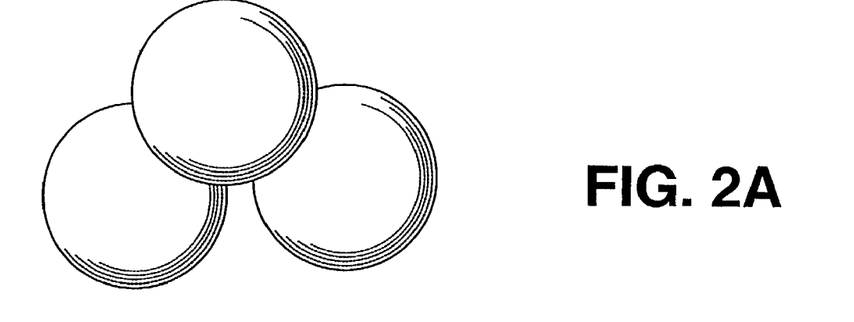
FIGS. 2a, 2b, and 2c are examples of possible embodiments of the present invention.
Figure 2B:
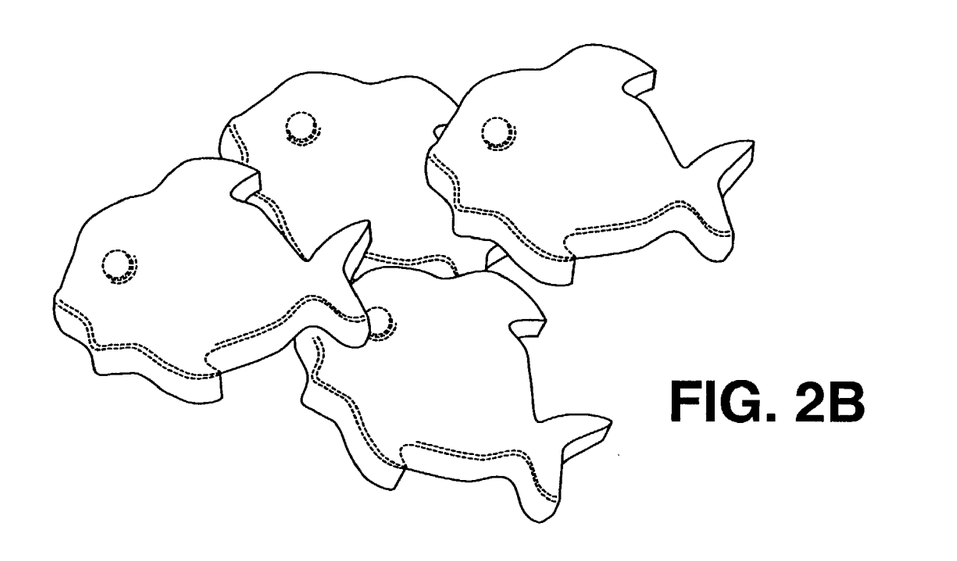
Figure 2C:
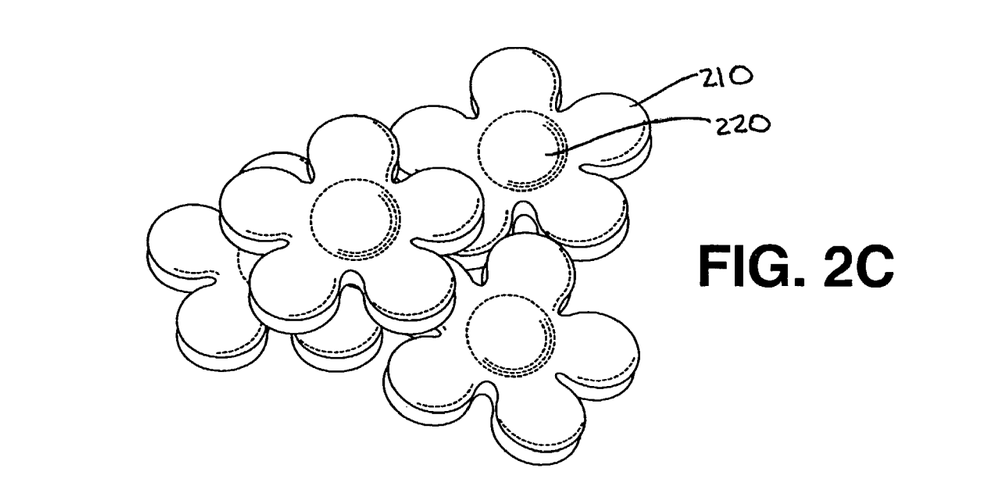

The nozzle 106 of the extruder can be any desired shape and can be designed to produce a cleansing product of any desired shape. For example, the nozzle 106 can be a slot, such as can produce a flat sheet of extrudate. The final product shape can then be punched from the extrudate, producing a flat cleansing product having the desired shape. If desired, in such an embodiment, additional details or shaping can be added using any known figure shaping process, such as, for example, an embossing process. The flat fish figure illustrated in FIG. 2B and the flowers shown in FIG. 2C illustrate two possible embodiments of relatively flat product shapes, though any shapes could be formed: stars, moons, sun, clouds, animals, letters, cartoon characters, just to name a few.

Alternatively, the extruder nozzle 106 could have a more complex cross-sectional shape, and the final product shape could be formed by merely slicing the extrudate into the desired lengths as it exits the extruder. Additional molding of the extrudate can also be done to produce more complex, three dimensional shapes, as desired. For example, spheres, such as those illustrated in FIG. 2A could be formed. Three dimensional shapes could also be formed using other known processing techniques, such as, for example injection molding processing techniques. Any desired shapes could be formed. For example, the individual cleansing products could resemble common items such as food products, for instance popcorn or candy, crayons, clouds, cotton balls, and the like.

In one embodiment of the present invention, several individual-sized cleansing products can be combined together to form one large conglomerate object. For example, several spherical products could be connected, such as with a small amount of water at the point of contact, to meld the pieces together to form a single combined arrangement to resemble, for example, a mass of interlocking soap bubbles or a cluster of grapes. A single individual product piece could then be pulled from the cluster when used to wash. The individual shapes, for example individual 'bubbles' or 'grapes' could additionally be of a variety of colors and fragrances, characteristics which could either be apparent when the product is dry or alternatively could become apparent only when the product becomes wet. More complex shapes could also be formed of multiple different shapes attached together, such as large flowers, animals, or the like, from which a single piece can be pulled off for washing.

In one embodiment of the present invention, a co-extrusion process can be used, and the cleansing product thus produced can be a multi-zone cleansing product with one zone of a different material than other zones. For example, a cleansing product can be produced in a desired shape, such as a flower as illustrated in FIG. 2C, with the outer zone of the flower 210 one type of extrudate, and the inner zone of the flower 220 an extrudate of different characteristics, such as a different color, for example. Alternatively, one of the zones could be formed of a different material altogether, other than the foam extrudate of the present invention. In one embodiment, as the two zones disintegrate and their components mix during scrubbing, characteristics of the product, such as the color and/or fragrance, for example, could change.

Reference now will be made to various embodiments of the invention, examples of which are set forth below. Each example is provided by way of explanation of the invention, not as a limitation of the invention. In fact, it will be apparent to those skilled in the art that various modifications and variations can be made of this invention without departing from the scope or spirit of the invention.

EXAMPLE 1

Mixtures were prepared in a Hobart® model A120-2 mixer and fed to a conical twin screw extruder. The mixtures were prepared with component amounts as described in Table 1, below. The extruder was operated at a variety of screw speeds and nozzle exit temperatures as indicated in the table. The soap base was a synthetic detergent combination of Nacconol® available from the Stepan Corporation (average particle size of less than about 1 mm) and Jordapon®) CL prilled isethionate available from the BASF Corporation (average particle size of less than about 1 mm). The nozzle was circular with a diameter of 3 mm for all samples. The characteristics of the lather were determined through a subjective determination by a panel of researchers and classified as defined as follows:

Poor: Little to no bubbles; very watery, thin soap suds.
Fair: Small and few bubbles; watery, thin soap suds.
Good: More and larger bubbles than those in Fair classification; some body to the soap suds
Great: Many bubbles, thick soap suds The remaining particulate matter after disintegration of the foam was classified as follows through visual assessment of amount/number of particles and size of particle on a subjective basis.

Very fine: Little to no grit with almost unnoticeable size of grit.
Fine: Very small, very fine grit.
Medium: Noticeably sized grit.
Large: Larger, very noticeable grit or lumps of cleanser.
Whole: Little disintegration; large, almost whole lump of cleanser.

TABLE 1

| Sample | 1 | 2 | 3 | 4 | 5 | 6 | 7 | 8 |
|---|---|---|---|---|---|---|---|---|
| Soap base (g) | 75 | 85 | 95 | 105 | 115 | 115 | 115 | 115 |
| talc (g) | 40 | 40 | 40 | 40 | 40 | 40 | 40 | 40 |
| PVA (g) | 40 | 40 | 40 | 40 | 40 | 40 | 40 | 40 |
| Destructured Starch (g) | 135 | 135 | 135 | 135 | 135 | 135 | 135 | 135 |
| Dextrin (g) | 200 | 200 | 200 | 200 | 200 | 200 | 200 | 200 |
| Ethanol (g) | 40 | 40 | 40 | 40 | 40 | 40 | 40 | 40 |
| Natural Starch (g) | 20 | 20 | 20 | 20 | 20 | 20 | 20 | 20 |
| Temperature At Nozzle (° C.) | 165 | 165 | 165 | 165 | 165 | 170 | 170 | 170 |
| Screw Speed (RPM) | 160 | 160 | 160 | 160 | 160 | 190 | 160 | 180 |
| Foam Diameter (mm) | 7.82 | 8.82 | 8.5 | 7.21 | 4.41 | 7 | 6.17 | 6.95 |
| Lather | Good | Fair | Great | Great | Good | Fair | Fair | Good |
| Remaining Particulate | Fine | Med | Very Fine | Very Fine | Med | Med | Large | Fine |

EXAMPLE 2

Mixtures were prepared and extruded as in Example 1, above. Component amounts added to the mixture and product characterizations are described in Table 2, below.

TABLE 2

| SAMPLE | 9 | 10 | 11 | 12 | 13 | 14 | 15 | 16 | 17 | 18 |
|---|---|---|---|---|---|---|---|---|---|---|
| Soap base (g) | 115 | 115 | 115 | 115 | 115 | 115 | 115 | 115 | 115 | 115 |
| talc (g) | 40 | 40 | 40 | 40 | 40 | 40 | 40 | 40 | 120 | 120 |
| PVA (g) | 40 | 40 | 40 | 40 | 40 | 40 | 40 | 40 | 40 | 40 |
| Destructured Starch (g) | 135 | 135 | 65 | 65 | 100 | 100 | 135 | 135 | 135 | 135 |
| Dextrin (g) | 200 | 200 | 200 | 200 | 200 | 200 | 250 | 250 | 40 | 40 |
| Ethanol (g) | 40 | 40 | 40 | 40 | 40 | 40 | 40 | 40 | 40 | 40 |
| Natural Starch (g) | 20 | 20 | 90 | 90 | 55 | 55 | 20 | 20 | 100 | 100 |
| Temperature At Nozzle (° C.) | 170 | 170 | 170 | 170 | 170 | 170 | 170 | 170 | 170 | 170 |
| Screw Speed (RPM) | 160 | 190 | 160 | 190 | 160 | 190 | 160 | 190 | 160 | 190 |
| Foam Diameter (mm) | 6.8 | 8.22 | 6.77 | 6.17 | 6.47 | 7.2 | 8.62 | 10.09 | 5.3 | 5.2 |
| Lather | Poor | Fair | Good | Good | Good | Good | Poor | Good | Poor | Good |

TABLE 2-continued

| SAMPLE | 9 | 10 | 11 | 12 | 13 | 14 | 15 | 16 | 17 | 18 |
|---|---|---|---|---|---|---|---|---|---|---|
| Remaining Particulate | Med | Med | Fine | Very Fine | Fine | Fine | Large | Large | Whole | Whole |

EXAMPLE 3

Mixtures were prepared and extruded as in Example 1, above. Component amounts added to the mixture and product characterizations are described in Table 3, below. Variations in nozzle diameter were used in the samples, as shown below in the table.

TABLE 3

| Sample | 19 | 20 | 21 | 22 | 23 | 24 | 25 |
|---|---|---|---|---|---|---|---|
| Soap base (g) | 115 | 115 | 115 | 115 | 115 | 115 | 115 |
| talc (g) | 40 | 40 | 40 | 40 | 40 | 40 | 40 |
| PVA (g) | 40 | 40 | 40 | 40 | 40 | 40 | 40 |
| Destructured Starch (g) | 65 | 65 | 65 | 65 | 65 | 65 | 30 |
| Dextrin (g) | 200 | 200 | 200 | 200 | 200 | 200 | 200 |
| Ethanol (g) | 40 | 40 | 40 | 40 | 40 | 40 | 40 |
| Natural Starch (g) | 20 | 20 | 20 | 0 | 55 | 90 | 20 |
| Temperature At Nozzle (° C.) | 165 | 165 | 165 | 165 | 165 | 165 | 165 |
| Screw Speed (RPM) | 160 | 160 | 160 | 160 | 160 | 160 | 160 |
| Nozzle (mm) | 7 | 5 | 3 | 3 | 3 | 3 | 3 |
| Remaining Particulate | Very Fine | Med | Med | Fine | Very Fine | Fine | Very Fine |
| Lather | Good | Good | OK | OK | Good | Good | Good |

EXAMPLE 4

Mixtures were prepared and extruded as in Example 1, above. Component amounts added to the mixture and product characterizations are described in Table 4, below.

TABLE 4

| Sample | 26 | 27 | 28 | 29 | 30 | 31 | 32 | 33 | 34 | 35 | 36 | 37 | 38 | 39 | 40 | 41 |
|---|---|---|---|---|---|---|---|---|---|---|---|---|---|---|---|---|
| Soap Base (g) | 95 | 95 | 95 | 95 | 95 | 110 | 110 | 110 | 110 | 110 | 115 | 115 | 115 | 115 | 115 | 95 |
| Talc (g) | 40 | 40 | 40 | 40 | 40 | 40 | 40 | 40 | 40 | 40 | 40 | 40 | 40 | 40 | 40 | 40 |
| PVA (g) | 40 | 40 | 40 | 40 | 40 | 40 | 40 | 40 | 40 | 40 | 40 | 40 | 40 | 40 | 40 | 40 |
| Destructured Starch (g) | 65 | 100 | 135 | 135 | 135 | 65 | 100 | 135 | 135 | 135 | 65 | 100 | 135 | 135 | 135 | 135 |
| Dextrin (g) | 200 | 200 | 200 | 200 | 200 | 200 | 200 | 200 | 200 | 200 | 200 | 200 | 200 | 200 | 200 | 200 |
| Ethanol (g) | 40 | 40 | 40 | 40 | 40 | 40 | 40 | 40 | 40 | 40 | 40 | 40 | 40 | 40 | 40 | 40 |
| Natural Starch (g) | 20 | 20 | 20 | 55 | 90 | 20 | 20 | 20 | 55 | 90 | 20 | 20 | 20 | 55 | 90 | 20 |
| Temperature At Nozzle (° C.) | 165 | 165 | 165 | 165 | 165 | 165 | 165 | 165 | 165 | 165 | 165 | 165 | 165 | 165 | 165 | 165 |
| Screw Speed (RPM) | 160 | 160 | 160 | 160 | 160 | 160 | 160 | 160 | 160 | 160 | 160 | 160 | 160 | 160 | 160 | 160 |
| Lather | OK | OK | OK | OK | Gd | Gd | Gd | OK | OK | Gd | Gd | Gd | OK | OK | OK | OK |
| Remaining Particulate | d | Med | Fine | M/L | Fine | Med | Fine | Med | Med | Med | Very Fine | Fine | Large | Med | Large | L/M |

EXAMPLE 5

Mixtures were prepared and extruded as in Example 1, above. Component amounts added to the mixture and product characterizations are described in Table 5, below.

TABLE 5

| Sample | 42 | 43 | 44 | 45 | 46 | 47 | 48 | 49 |
|---|---|---|---|---|---|---|---|---|
| Nacconol ® (g) | 98 | 98 | 98 | 98 | 98 | 98 | 98 | 98 |
| Jordapon ® (g) | 17 | 17 | 17 | 17 | 17 | 17 | 17 | 17 |
| Talc (g) | 40 | 40 | 40 | 40 | 40 | 40 | 40 | 40 |
| PVA (g) | 40 | 40 | 40 | 40 | 40 | 40 | 40 | 40 |
| Destructured Starch (g) | 65 | 65 | 65 | 65 | 65 | 65 | 65 | 65 |
| Dextrin (g) | 200 | 200 | 200 | 200 | 200 | 200 | 200 | 200 |
| Ethanol (g) | 40 | 40 | 40 | 40 | 40 | 40 | 40 | 40 |
| Natural Starch (g) | 20 | 20 | 20 | 20 | 20 | 20 | 20 | 20 |
| Fragrance (g) | None | None | None | None | None | None | 5 | 10 |
| Temperature At Nozzle (° C.) | 165 | 165 | 165 | 165 | 165 | 165 | 165 | 165 |
| Screw Speed (RPM) | 160 | 145 | 135 | 120 | 160 | 160 | | |
| Nozzle (mm) | 3 | 3 | 3 | 3 | 2 | 7 | | |
| Product Diameter (mm) | 5.3 | 9 | 7 | 5 | | 8.5 | 3.5 | 4.25 |
| Dissoloves | Ok | Good | Ok | Ok | | Poor | Ok | Poor |

As can be seen by the results of the above described examples, the process of the present invention can produce an extruded cleansing product with a variety of characteristics. As such, the process can be adapted without undue experimentation to produce an extruded cleansing product according to any desired parameters such as, for example, rate of dissolution, suds characteristics upon dissolution, abrasiveness of the cleanser, aggressiveness of the cleanser, and the like.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An extruded foam cleansing product for washing hands comprising an extruded foam structure that is configured to disintegrate during hand washing, the foam structure being formed by expanding a mixture together through an extruder, the mixture including:
   a water soluble disintegrant;
   a natural starch;
   a soap base;
   a nucleating agent;
   destructured starch;
   a water soluble polymer being present in the extruded foam structure in an amount from about 5% to about 10% by weight; and
   wherein said foam structure disintegrates when the foam structure is in contact with water such that the soap base is released from the foam structure as the foam structure disintegrates.

2. The cleansing product of claim 1, comprising between about 5% and about 10% by weight nucleating agent.

3. The cleansing product of claim 1, wherein the nucleating agent comprises talc.

4. The cleansing product of claim 3, wherein the talc comprises food grade talc.

5. The cleansing product of claim 1, wherein the water soluble polymer comprises polyvinyl alcohol.

6. The cleansing product of claim 1, wherein the product comprises between about 2% and about 10% natural starch.

7. The cleansing product of claim 1, wherein the product comprises between about 20% and about 65% by weight water soluble disintegrant.

8. The cleansing product of claim 1, wherein the water soluble disintegrant comprises dextrin.

9. The cleansing product of claim 8, wherein the water soluble disintegrant comprises maltodextrin.

10. The cleansing product of claim 1, wherein the foam disintegrates in less than about 2 minutes.

11. The cleansing product of claim 1, wherein the foam disintegrates over a period of time which is dependent upon the temperature of the water.

12. The cleansing product of claim 1, wherein the cleansing product comprises between about 10% and about 30% by weight soap base.

13. The cleansing product of claim 1, wherein said soap base comprises a synthetic detergent.

14. The cleansing product of claim 1, wherein said soap base comprises a fatty acid soap.

15. The cleansing product of claim 1, further comprising an additive selected from the group consisting of dyes, fragrances, emollients, vitamins, antioxidants, and mixtures thereof.

16. The cleansing product of claim 1, further comprising an encapsulated additive.

17. The cleansing product of claim 1, further comprising an abrasion enhancing additive.

18. The cleansing product of claim 1, wherein said product comprises less than about 25% by weight destructured starch.

19. An extruded foam cleansing product for washing hands formed from a mixture comprising an extruded foam structure that is configured to disintegrate during hand washing, the foam structure being formed by expanding a mixture together through an extruder, the mixture including:
   a water soluble disintegrant, the water soluble disintegrant being present in the extruded foam structure in an amount from about 20% to about 65% by weight, and wherein the water soluble disintegrant comprises dextrin;
   a nucleating agent;
   a soap base;
   a natural starch;
   a water soluble thermoplastic polymer being present in the extruded foam structure in an amount from about 5% to about 10% by weight;
   a blowing agent; and
   wherein said foam structure disintegrates when the foam structure is in contact with water such that the soap base is released from the foam structure as the foam structure disintegrates.

20. The cleansing product of claim 19, further comprising destructured starch.

21. The cleansing product of claim 20, wherein the mixture comprises less than about 25% by weight destructured starch.

22. The cleansing product of claim 19, wherein the mixture comprises between about 20% and about 50% by weight water soluble disintegrant, between about 10% and about 30% by weight soap base selected from the group consisting of synthetic detergents, fatty acid soaps, and mixtures thereof, between about 5% and about 10% water soluble thermoplastic polymer, between about 5% and about 10% by weight of a blowing agent, between about 5% and about 10% by weight nucleating agent, between 0% and about 25% destructured starch, and between about 2% and about 10% natural starch.

23. The cleansing product of claim 22, wherein the foam disintegrates in less than about 2 minutes.

24. The cleansing product of claim 22, wherein the foam disintegrates upon contact with water.

25. The cleansing product of claim 22, wherein said foam disintegrates over a period of time that is dependent upon the temperature of the water.

26. The cleansing product of claim 19, wherein the blowing agent comprises an alcohol.

27. The cleansing product of claim 26, wherein the alcohol comprises ethanol.

28. The cleansing product of claim 19, wherein the water soluble disintegrant comprises maltodextrin.

29. The cleansing product of claim 19, wherein the nucleating agent is food grade talc.

30. The cleansing product of claim 19, wherein the water soluble thermoplastic polymer comprises polyvinyl alcohol.

31. The cleansing product of claim 19, said mixture further comprising an additive selected from the group consisting of dyes, fragrances, emollients, vitamins, antioxidants, and mixtures thereof.

32. The cleansing product of claim 19, said mixture further comprising an encapsulated additive.

33. The cleansing product of claim 19, said mixture further comprising an abrasion enhancing additive.

34. The cleansing product as defined in claim 1, wherein the mixture further comprises a blowing agent, the blowing agent comprising an alcohol.

35. The cleansing product of claim 34, wherein the blowing agent comprises ethanol.

36. An extruded foam cleansing product for washing hands comprising an extruded foam structure that is configured to disintegrate during hand washing, the foam structure being formed by expanding a mixture together through an extruder, the mixture including:
- a water soluble disintegrant;
- a natural starch;
- a soap base;
- a nucleating agent comprising a food grade talc;
- a water soluble polymer being present in the extruded foam structure in an amount from about 5% to about 10% by weight; and
- wherein said foam structure disintegrates when the foam structure is in contact with water such that the soap base is released from the foam structure as the foam structure disintegrates.

37. An extruded foam cleansing product for washing hands comprising an extruded foam structure that is configured to disintegrate during hand washing, the foam structure being formed by expanding a mixture together through an extruder, the mixture including:
- a water soluble disintegrant comprising a dextrin;
- a natural starch;
- a soap base;
- a nucleating agent;
- a water soluble polymer being present in the extruded foam structure in an amount from about 5% to about 10% by weight; and
- wherein said foam structure disintegrates when the foam structure is in contact with water such that the soap base is released from the foam structure as the foam structure disintegrates.

* * * * *